United States Patent [19]
Albright, Jr.

[11] Patent Number: 5,629,449
[45] Date of Patent: *May 13, 1997

[54] CONTROLLED FEED PROCESS FOR MAKING 3,5-DIAMINOBENZOTRIFLUORIDE

[75] Inventor: David E. Albright, Jr., Niagara Falls, N.Y.

[73] Assignee: Occidental Chemical Corporation, Niagara Falls, N.Y.

[*] Notice: The term of this patent shall not extend beyond the expiration date of Pat. No. 5,347,057.

[21] Appl. No.: 930,942

[22] Filed: Aug. 17, 1992

Related U.S. Application Data

[63] Continuation-in-part of Ser. No. 685,106, Apr. 15, 1991, Pat. No. 5,347,052.

[51] Int. Cl.$^6$ ................................................. C07C 209/32
[52] U.S. Cl. ...................... 564/417; 564/415; 564/416; 564/422; 564/423
[58] Field of Search ........................... 564/415, 417, 564/423, 422

[56] References Cited

U.S. PATENT DOCUMENTS

| | | | |
|---|---|---|---|
| 3,073,865 | 1/1963 | Spiegler | 564/417 |
| 5,144,076 | 9/1992 | Krishnamurti et al. | 564/417 |

FOREIGN PATENT DOCUMENTS

| | | | |
|---|---|---|---|
| 38465 | 10/1981 | European Pat. Off. | 564/417 |
| 91119450.4 | 11/1991 | European Pat. Off. | |

OTHER PUBLICATIONS

J. Chem. Soc. Perkin Trans. II 1986 pp. 187–192, 1986.

*Primary Examiner*—Shailendra Kumar
*Attorney, Agent, or Firm*—Richard D. Fuerle; Arthur S. Cookfair

[57] ABSTRACT

Disclosed is a method of making 3,5-diaminobenzotrifluoride from 4-chloro-3,5-dinitrobenzotrifluoride. A solution of 4-chloro-3,5-dinitrobenzotrifluoride in an alcohol is prepared. Separately, a slurry is prepared of a palladium catalyst on a suitable substrate, at least one equivalent of magnesium oxide per equivalent of 4-chloro-3,5-dinitrobenzotrifluoride, sufficient hydrogen-donating reducing agent to reduce the 4-chloro-3,5-dinitrobenzotrifluoride to 3,5-diaminobenzotrifluoride, and an amount of alcohol sufficient to make the slurry stirrable. The solution is added to the slurry with stirring at a rate that does not exceed the reaction rate of the 4-chloro-3,5-dinitrobenzotrifluoride so that no unreacted 4-chloro-3,5-dinitrobenzotrifluoride accumulates in the slurry. The reaction mixture is heated at about 75° to about 100° C.

17 Claims, No Drawings

CONTROLLED FEED PROCESS FOR MAKING 3,5-DIAMINOBENZOTRIFLUORIDE

This application is a CIP of application Ser. No. 07/685,106, filed Apr. 15, 1991, now U.S. Pat. No. 5,347,052.

This application is a continuation-in-part of application Serial No. 07/685,106, filed April 15, 1991, by David E. Albright, Jr., titled "Preparation of 3,5-Diaminobenzotrifluoride."

BACKGROUND OF THE INVENTION

This invention relates to a method of making 3,5-diaminobenzotrifluoride (DABTF) from 4-chloro-3,5-dinitrobenzotrifluoride (CDNBTF). In particular, it relates to a process in which a solution of CDNBTF is added at a controlled rate to a slurry of a palladium catalyst, magnesium oxide, and an alcohol solvent.

In U.S. patent application Ser. No. 07/685,106, there is described a process for preparing DABTF from CDNBTF by reacting the CDNBTF with hydrogen in the presence of magnesium oxide, a palladium catalyst, and methanol. While that process is successful in the laboratory, it has since been found that upon scaling up to quantities of three gallons or more, the yield falls, the solution becomes dark and gummy, and tars and other undesirable compounds form, making it difficult to isolate the product.

Analysis showed that the starting material, CDNBTF, was reacting with the product, DABTF, to produce a dimer according the equation

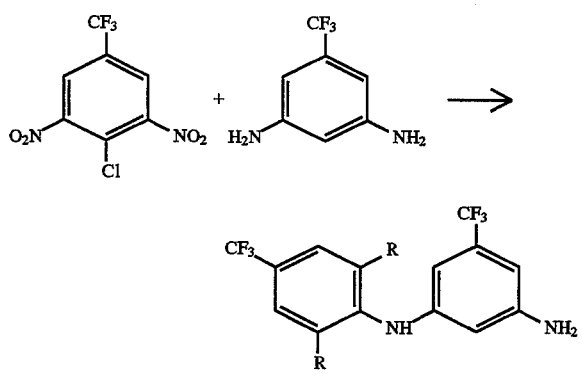

where R is $NH_2$ if the reaction is performed in the presence of hydrogen and a Pd/C catalyst and is $NO_2$ if hydrogen and the Pd/C catalyst are not present. Other undesirable but unidentified compounds also seemed to be present. In addition, dechlorination did not occur completely so that 4-chloro-3,5-diaminobenzotrifluoride (CDABTF) was also formed, apparently due to deactivation of the catalyst.

SUMMARY OF THE INVENTION

I have discovered that these scale-up problems can be overcome so that large quantities of DABTF can be produced from CDNBTF in yields in excess of 90% without the formation of tars and compounds that make the solution dark and gummy. I am able to accomplish this by adding a solution of the CDNBTF to a slurry of MgO and the catalyst at a rate that is no greater than the reaction rate of CDNBTF so that the CDNBTF does not accumulate in the reaction mixture. The absence of accumulated CDNBTF in the reaction mixture is the key to preventing the formation of these tars and other undesirable compounds.

DESCRIPTION OF THE INVENTION

In the process of this invention, a solution of CDNBTF, a commercially available chemical, is prepared in a suitable alcohol, preferably a 1-alkanol to $C_4$ (i.e., methanol, ethanol, n-propanol, or n-butanol). The preferred solvent is methanol as it is inexpensive and is more effective than the other alcohols. However, methanol vapor may spontaneously combust in the presence of the catalyst and air so precautions must be taken to exclude air when methanol is contacted with the catalyst; use of a water-wet catalyst is also advisable. The solution of CDNBTF in the alcohol can be saturated but more dilute solutions are preferred as that produces a higher yield and fewer side products. Preferably, the concentration of CDNBTF in the alcohol should be less than 0.3 g/mL and a solution of about 5 to about 30 wt % works well. It is not necessary to pre-heat the solution of CDNBTF, though it can be pre-heated if desired.

Separately, a reactor is charged with a palladium catalyst and magnesium oxide. The palladium is preferably on a suitable support such as carbon, barium sulfate, or alumina; carbon is preferred as it is most effective, easiest to recycle, and inexpensive. Typically, the catalyst is sold as 1 to 10 wt % palladium on carbon. It is preferable to use about 5 to about 10 wt % of the catalyst, based on CDNBTF weight, as less catalyst will result in a slower reaction and may lead to the formation of side products and more catalyst is unnecessary.

The reactor is also charged with magnesium oxide, MgO. At least one equivalent of magnesium oxide is required for each equivalent of CDNBTF and it is preferable to use excess magnesium oxide to insure a complete reaction. About one to about two equivalents magnesium oxide is preferable per equivalent CDNBTF.

The reactor is then purged with an inert gas to remove air. Nitrogen is preferable for this purpose, although argon or other inert gases could also be used. Sufficient alcohol is then added to the reactor to form a slurry with the palladium catalyst and the magnesium oxide.

The presence of a hydrogen-donating reducing agent is also required. Examples of suitable hydrogen-donating reducing agents include hydrogen gas and Raney nickel. Sufficient hydrogen-donating reducing agent should be present to provide at least seven moles of hydrogen per mole of CDNBTF. The preferred hydrogen-donating reducing agent is hydrogen gas as it is most effective. If hydrogen gas is used, the slurry of catalyst and magnesium oxide in the alcohol is stirred and purged with the hydrogen gas, preferably at a pressure of about 50 to 100 psi. Other reducing agents can be simply added to the slurry.

The slurry is heated to a temperature of about 75° to about 100° C. and is maintained within that temperature range during the addition of the CDNBTF. At lower temperatures the reaction is too slow and side products may be produced and higher temperatures are unnecessary and lead to high vapor pressures. Because the reaction is highly exothermic, it is usually not necessary to add additional heat during the reaction and occasionally cooling may even be necessary.

The critical step in the process of this invention is the addition of the solution of CDNBTF. The solution of CDNBTF must be added to the slurry with stirring at a rate that is slow enough to prevent the accumulation of CDNBTF in the reaction vessel. This can be accomplished if the reaction is rapid and the rate of addition is slow. In other words, the CDNBTF should be added at a rate that does not exceed its reaction rate. This normally requires one to two hours. While I do not wish to be bound by any theories, I believe that the process of this invention proceeds according to the following equation

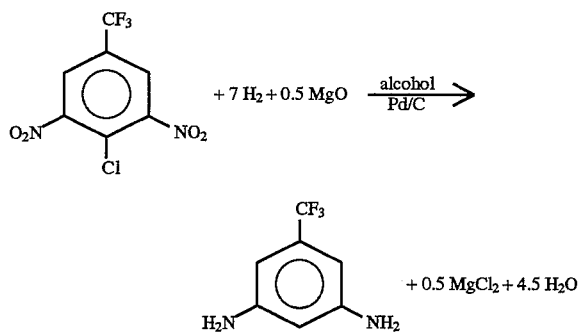

Since the nitro groups are reduced before the chlorine is removed, the reaction proceeds through the intermediate, CDABTF. The completion of the reaction can be determined by taking samples of the solution and testing for the presence of CDABTF using a gas chromatograph (GC). The reaction will normally proceed to at least 90% completion and 100% completion can be achieved under optimized conditions. When the reaction is finished, stirring is terminated and the solids are permitted to settle out. The solution containing the DABTF can then be decanted off. A centrifuge could also be used to separate the solution from the solids. It is preferable to leave a small amount of alcohol remaining in the reactor. Additional magnesium oxide and some (about 10%) fresh catalyst can then be added to the reactor to prepare a new batch of product.

The DABTF can be recovered as a solid precipitate from the alcohol in the decanted solution by distillation of the alcohol, which is recovered and recycled. The magnesium chloride formed in the hydrodechlorination reaction is very soluble in the alcohol solvent and will precipitate with the DABTF. It can be separated from the DABTF by extraction with water. Two consecutive extractions using 80 to 100 g. of water per 100 g. of molten DABTF near a temperature of 100° C. remove the magnesium chloride to less than 500 ppm. Since more than 95% of the magnesium chloride is removed by the first extraction, the water from the second extraction can be recycled to the first extraction of another batch. After water extraction, the molten crude DABTF (density 1.28 g/cc) is easily settled from the water which can then be cooled and decanted. The small amount of DABTF which is solubilized in the water (typically 2 g. per 100 cc of water) can be recovered by extraction with an organic solvent such as butyl acetate.

Pure DABTF can be produced from the crude material by distillation. If any CDABTF is left in the product, the resulting DABTF can be purified by selective precipitation of its hydrochloride salt (see U.S. Pat. No. 5,130,490, herein incorporated by reference). DABTF is useful in the production of high performance polyimides, polyamides, polyurethanes, and epoxies.

The following examples further illustrate this invention. Examples 8, 9, 11, and 12 specifically illustrate the claimed process and the other examples illustrate the chemistry of the claimed process.

EXAMPLE 1

This example illustrates the making of DABTF from CDNBTF in a variety of alcohols. Using a 500 mL Parr hydrogenator, 10 g. CDNBTF, 1.6 g. MgO, 1.2 g. of water-wet 5% Pd/C catalyst, and 100–120 mL of solvent were added and heated to 80° C. under 50 psig of hydrogen. The following table gives the alcohols used and the results of these experiments.

| Solvent | DABTF (g) | CDABTF (g) | DABTF Mass Yield (%) |
|---|---|---|---|
| Methanol | 6.29 | 0.00 | 97 |
| Ethanol | 5.91 | 0.44 | 91 |
| 1-propanol | 5.41 | 0.88 | 83 |
| Ethyl Acetate | 3.90 | 2.62 | 60 |
| Isopropanol | 4.02 | 2.53 | 62 |

EXAMPLE 2

Example 1 was repeated with methanol using various amounts of magnesium oxide. The following table gives the results.

| CDNBTF (g) | MgO (g) | DABTF (g) | CDABTF (g) | DABTF Yield (%) |
|---|---|---|---|---|
| 10 | 3.0 (4 eq.) | 6.10 | 0.28 | 94 |
| 10 | 1.6 (2 eq.) | 6.29 | 0.00 | 97 |
| 10 | 0.8 (1 eq.) | 5.81 | 0.04 | 89 |
| 10 | 0.0 (0 eq.) | 2.85 | 0.76 | 44 |
| 20 | 3.2 (2 eq.) | 12.9 | 0.06 | 99 |

EXAMPLE 3

Example 1 was repeated using different amounts of catalyst and methanol with 10 g. of CDNBTF. The following table gives the results.

| Methanol (mL) | Pd/C (g) | DABTF (g) | CDABTF (g) | DABTF Mass Yield (%) |
|---|---|---|---|---|
| 100 | 1.2 | 6.29 | 0.00 | 97 |
| 60 | 1.2 | 5.65 | 0.08 | 87 |
| 60 | 0.8 | 5.84 | 0.48 | 90 |
| 100 | 0.8 | 6.23 | 0.03 | 96 |

The above table shows that better results were achieved with the more dilute solution and that 0.8 g of catalyst was sufficient.

EXAMPLE 4

Example 1 was repeated with methanol using various bases. The following table gives the results.

| CDNBTF (g) | Base | DABTF (g) | CDABTF (g) | DABTF Mass Yield (%) |
|---|---|---|---|---|
| 10 | MgO | 6.29 | 0.00 | 97 |
| 10 | CaO | 0.90 | 0.86 | 14 |
| 10 | None | 2.85 | 0.76 | 44 |
| 5 | $Na_2CO_3$ | 2.04 | 0.07 | 63 |
| 10 | NaOH | 1.99 | 0.11 | 31 |
| 10 | NAOH* | 3.62 | 2.45 | 56 |

*Added after the initial reduction of the nitro groups without a base present to eliminate the displacement of the labile Cl.

These experiments show that magnesium oxide is the only base that is effective in this reaction.

EXAMPLE 5

The reactor was charged with 6.32 g. CDABTF and 100 mL methanol. Runs were carried out for 20 minutes using 10 wt % catalyst and different temperatures and pressures. The following table gives the results.

| T (°C.) | P (psia) | MgO (eq.) | Conversion (%) |
|---|---|---|---|
| 23 | 29 | 1.5 | 15.6 |
| 23 | 62 | 1.5 | 13.8 |
| 60 | 29 | 1.5 | 58.7 |
| 80 | 29 | 1.5 | 86.4 |
| 90 | 29 | 1.5 | 98.5 |
| 90 | 29 | 1.16 | 96.5 |

The above table shows that temperatures over 60° C. are required for a satisfactory conversion of CDABTF to DABTF.

EXAMPLE 6

In this example, the reaction was scaled up to a larger reactor. A three gallon Pfaudler reactor was charged with 700 g. of CDNBTF, 7000 mL methanol, 104 g. magnesium oxide, and 84 g. water-wet Pd/C catalyst. The reaction was carried out under 40 to 50 psi of hydrogen and near 80° C. After one hour, a gas chromatogram (GC) sample showed the presence of 9.4 area % CDABTF. After an additional four hours, GC analysis still showed the presence of 9.1 area % CDABTF. This indicated that the catalyst had been deactivated and that no significant further reaction was occurring. GC internal standard analysis of the filtered reaction product showed the formation of 382.3 g. DABTF and 29.6 g. CDABTF. However, the product was highly colored and solvent evaporation showed the presence of a tar-like side product which had not been seen in the small scale reactions. This tar-like substance greatly hindered all further processing, including catalyst recovery.

EXAMPLE 7

Example 6 was repeated using 700 g. CDNBTF, 7000 mL methanol, 100 g. MgO and 100 g. of water-wet palladium on carbon catalyst in 70 to 85 psi hydrogen and 85°–100° C. GC analysis of the reaction product showed removal of the CDBTF to less than 3%. However, tar formation also increased and the mass yield of DABTF was only about 75%.

EXAMPLE 8

The reaction of Example 7 was repeated except that the reactor was modified so that a concentrated methanol solution of CDNBTF could be metered into the reactor. The reactor was charged with 2900 mL of methanol, 104 g. MgO and 100 g. of water-wet Pd/C catalyst. The charge was heated and agitated under hydrogen pressure and the addition of 700 g. CDNBTF and 3000 mL of methanol was carried out over 90 minutes at a rate below the reaction rate of the CDNBTF, so that no CDNBTF accumulated. The reaction was under 50 psi hydrogen at about 70°–80° C. Analysis of the reaction product showed that about 12% of the CDABTF intermediate remained unreacted. However, the product was clear with no trace of any tar side product.

EXAMPLE 9

Example 8 was repeated using an initial charge of 3000 mL of methanol, 100 g. MgO, and 130 g. of water-wet Pd/C catalyst. The mixture was heated and agitated under hydrogen pressure and the addition of 1100 g. CDNBTF and 3500 mL of methanol was carried out over several hours. The rate of addition of the CDNBTF was less than its reaction rate and no CDNBTF accumulated. At the end of the CDABTF intermediate addition, more than 5 wt % CDNBTF remained unconverted. Continuation of agitation and heating between 80°–90° C. over several hours resulted in the complete removal of the CDABTF intermediate. GC analysis showed the formation of 620 g. of pure DABTF (87 wt % mass yield). The reaction products were initially water white but turned amber after exposure to air. No trace of tar side products was present.

EXAMPLE 10

The reactor was charged with 2700 mL of methanol, 67 g. of magnesium oxide, and only 15 g. of water-wet Pd/C catalyst. 750 g. of CDNBTF in 3000 mL of methanol was then slowly fed over 157 minutes. The temperature was maintained below 60° C. and the hydrogen pressure was kept between 40 and 60 psig. These conditions resulted in incomplete conversion and produced many side products which hindered product recovery.

EXAMPLE 11

A slurry containing 75 g. of water-wet Pd/C and 75 g. of magnesium oxide in 2000 mL of methanol was maintained near 80° C. under a hydrogen pressure of 90 psig. A dilute solution of 400 g. of CDNBTF in 3000 mL of methanol was added to the reactor over the course of 1 hour so that no starting material accumulated. Following the feed addition, the CDABTF intermediate concentration was approximately 20 percent. Continued agitation for another 6 hours achieved complete conversion of the remaining CDABTF intermediate to the DABTF product. The reaction products were colorless, very pure and easy to process. Distillation of the product proceeded readily with less than 3 percent of the material lost in the still bottoms. The ease of processing the dilute solution makes this an attractive option for dimer minimization and yield improvement. Coupling the dilute solution feed with a slower feed rate should provide the best hydrogenation results.

EXAMPLE 12

To achieve catalyst recycle in the 3 gallon Pfaudler reactor, solids from each completed hydrogenation were allowed to settle to the reactor bottom and the supernatant liquid containing the DABTF product was siphoned off for processing. Enough liquid was allowed to remain in the reactor to provide a starting slurry for the next batch. Make-up catalyst and MgO were added, the slurry was heated and agitated under hydrogen pressure, and then the next batch of CDNBTF solution was reacted with controlled feed. Five consecutive 3 gallon Pfaudler batches were carried to complete conversion using the Pd/C catalyst from the previous batch plus about 15 percent fresh catalyst make-up. The following table lists the charges and results for each experiment.

| Batch | Controlled Feed Solution | Charged to Pfaudler Prior to Batch | | | |
|---|---|---|---|---|---|
| | | MgO | Pd/C | MeOH | Conversion |
| 1 | 750 g CDNBTF in 3100 mL MeOH | 134 g | 100 g | 4000 mL | 100% |
| 2 | 750 g CDNBTF in 3000 mL MeOH | 50 g | 20 g | 0 | 100% |

-continued

| Batch | Controlled Feed Solution | Charged to Pfaudler Prior to Batch | | | Conversion |
|---|---|---|---|---|---|
| | | MgO | Pd/C | MeOH | |
| 3 | 750 g CDNBTF in 3000 mL MeOH | 60 g | 15 g | 0 | 100% |
| 4 | 750 g CDNBTF in 3000 mL MeOH | 56 g | 10 g | 0 | 100% |
| 5 | 750 g CDNBTF in 3000 mL MeOH | 56 g | 15 g | 0 | 100% |

Note: Pd/C charged is approximately 50% water by mass.

The controlled feed solution was added slowly so that no accumulation of the CDNBTF occurred.

No significant decrease in catalyst activity was observed over the course of the 5 consecutive runs. GC analysis of the final products showed that the CDABTF intermediate was reduced to negligible levels in each batch. This level of CDABTF removal would normally require about 75 to 100 g. of water-wet Pd/C for each batch for a total of 375 to 500 g. of 5% Pd/C (50% water). However, by recycling the catalyst from the previous batch, these runs required only 160 g. of Pd/C catalyst. Since no catalyst deactivation was observed, a greater reduction in catalyst usage is likely possible.

I claim:

1. A method of making 3,5-diaminobenzotrifluoride comprising:
   (1) preparing a solution of 4-chloro-3,5-dinitrobenzotrifluoride in a 1-alkanol;
   (2) preparing a slurry which comprises
      (a) a palladium catalyst on a suitable substrate;
      (b) at least one equivalent of magnesium oxide per equivalent of said 4-chloro-3,5-dinitrobenzotrifluoride;
      (c) sufficient hydrogen-donating reducing agent to reduce said 4-chloro-3,5-dinitrobenzotrifluoride to said 3,5-diaminobenzotrifluoride; and
      (d) an amount of said alkanol sufficient to make said slurry stirrable;
   (3) adding said solution to said slurry with stirring at a rate that does not exceed the reaction rate of said 4-chloro-3,5-dinitrobenzotrifluoride.

2. A method according to claim 1 wherein said alkanol is methanol.

3. A method according to claim 1 wherein the concentration of said 4-chloro-3,5-dinitrobenzotrifluoride in said alkanol is less than 0.3 g/mL.

4. A method according to claim 1 wherein the concentration of said 4-chloro-3,5-dinitrobenzotrifluoride in said alkanol is about 5 to about 30 wt %.

5. A method according to claim 1 wherein the mixture of said slurry and said solution are heated to about 75 to about 100° C.

6. A method according to claim 1 wherein said substrate is carbon.

7. A method according to claim 1 wherein the amount of magnesium oxide is 1 to about 2 equivalents per equivalent of said 4-chloro-3,5-dinitrobenzotrifluoride.

8. A method according to claim 1 including the additional last steps of letting solids settle and decanting off said solution.

9. A method according to claim 1 wherein said hydrogen-donating reducing agent is hydrogen under a pressure of about 50 to about 100 psi.

10. A method according to claim 1 wherein said catalyst is 1 to 10 wt % palladium on carbon and about 5 to about 10 wt % of said catalyst is used, based on 4-chloro-3,5-dinitrobenzotrifluoride.

11. A controlled feed process for making 3,5-diaminobenzotrifluoride from 4-chloro-3,5-dinitrobenzotrifluoride comprising:
   (1) preparing a solution in methanol of less than about 0.3 g/mL of 4-chloro-3,5-dinitrobenzotrifluoride;
   (2) preparing, in a reactor, a slurry which comprises
      (a) a catalytic amount of a palladium on carbon catalyst;
      (b) 1 to about 2 equivalents of MgO per equivalent of said 4-chloro-2,5-dinitrobenzotrifluoride; and
      (c) sufficient methanol to form said slurry;
   (3) purging said reactor with an inert gas;
   (4) admitting to said reactor under a pressure of about 50 to about 100 psi at least about 7 moles of hydrogen gas per mole of said 4-chloro-2,5-dinitrobenzotrifluoride;
   (5) adding said solution to said reactor at a rate sufficiently slow to prevent the accumulation of unreacted 4-chloro-3,5-dinitrobenzotrifluoride; and
   (6) maintaining the temperature in said reactor at about 75° to about 100° C.

12. A controlled feed process according to claim 11 wherein the concentration of said 4-chloro-3,5-dinitrobenzotrifluoride in said alcohol is about 5 to about 30 wt %.

13. A controlled feed process according to claim 11 wherein said catalyst is 1 to 10 wt % palladium on carbon and about 5 to about 10 wt % of said catalyst is used, based on 4-chloro-3,5-dinitrobenzotrifluoride.

14. A controlled feed process according to claim 11 including the additional last steps of letting solids settle in said reactor and decanting off said solution.

15. A controlled feed process according to claim 11 wherein said inert gas is nitrogen.

16. A method of making 3,5-diaminobenzotrifluoride comprising
   (1) preparing a solution in methanol of about 5 to about 30% by weight 4-chloro-3,5-dinitrobenzotrifluoride;
   (2) charging a reactor with
      (a) about 1 to about 2 equivalents of magnesium oxide per mole of said 4-chloro-3,5-dinitrobenzotrifluoride; and
      (b) about 5 to about 10% by weight of a catalyst comprising about 1 to about 10% by weight palladium on carbon;
   (3) purging said reactor with nitrogen;
   (4) adding sufficient methanol to said reactor to form a slurry of said magnesium oxide and said catalyst;
   (5) stirring said methanol, magnesium oxide, and catalyst in said reactor to form said slurry;
   (6) adding at least 7 moles of hydrogen to said reactor per mole of said 4-chloro-3,5-dinitrobenzotrifluoride at a pressure of about 50 to about 100 psi;
   (7) adding said solution to said reactor with stirring at a rate that does not exceed its reaction rate, so that unreacted 4-chloro-3,5-dinitrobenzotrifluoride does not accumulate in said reactor;
   (8) maintaining the temperature within said reactor at about 75° to about 100° C.;
   (9) after the addition of said solution, sampling the contents of said reactor to determine the progress of said reaction; and

(10) when at least 90% of the 4-chloro-3,5-aminobenzotrifluoride intermediate formed by said reaction has been converted into 3,5-diaminobenzotrifluoride, stopping said stirring, allowing solids to settle, and decanting said solution from said reactor.

17. A method according to claim 16 including the additional last steps of evaporating the methanol from said decanted solution and extracting magnesium chloride from the remaining solids with water.

* * * * *